(12) United States Patent
Huang et al.

(10) Patent No.: US 10,744,098 B2
(45) Date of Patent: Aug. 18, 2020

(54) SPRAY-DRIED SOLID-IN-OIL-IN-WATER DISPERSIONS FOR INHALATION OF ACTIVE PHARMACEUTICAL INGREDIENTS

(71) Applicants: Daniel Huang, Palo Alto, CA (US); Nagaraja Rao, San Leandro, CA (US); Trixie Tan, Belmont, CA (US); Danforth Miller, San Carlos, CA (US); Jeffry Weers, Belmont, CA (US)

(72) Inventors: Daniel Huang, Palo Alto, CA (US); Nagaraja Rao, San Leandro, CA (US); Trixie Tan, Belmont, CA (US); Danforth Miller, San Carlos, CA (US); Jeffry Weers, Belmont, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/121,161

(22) PCT Filed: Mar. 24, 2015

(86) PCT No.: PCT/IB2015/052151
§ 371 (c)(1),
(2) Date: Aug. 24, 2016

(87) PCT Pub. No.: WO2015/145353
PCT Pub. Date: Oct. 1, 2015

(65) Prior Publication Data
US 2017/0007547 A1    Jan. 12, 2017

Related U.S. Application Data

(60) Provisional application No. 61/971,232, filed on Mar. 27, 2014.

(51) Int. Cl.
*A61K 9/50* (2006.01)
*A61K 9/00* (2006.01)
(Continued)

(52) U.S. Cl.
CPC .......... *A61K 9/5089* (2013.01); *A61K 9/0075* (2013.01); *A61K 9/5015* (2013.01);
(Continued)

(58) Field of Classification Search
None
See application file for complete search history.

(56) References Cited

U.S. PATENT DOCUMENTS

2012/0141531 A1* 6/2012 Coulter .................. A61K 9/107
424/236.1
2014/0302147 A1* 10/2014 Hartman .............. A61K 9/1617
424/489

FOREIGN PATENT DOCUMENTS

| WO | 2001/85136 A2 | 11/2001 |
| WO | 2012/106575 A1 | 8/2012 |

* cited by examiner

*Primary Examiner* — Isis A Ghali
(74) *Attorney, Agent, or Firm* — Michael Mazza; Guy Tucker

(57) ABSTRACT

Embodiments of the invention relate to particulate agents and compositions comprising particulate agents for inhalation, and methods for preparing such particulate agents and compositions for inhalation, as well as therapeutic methods. Embodiments of the method comprise preparing an emulsion by combining an oil phase dispersion of hydrophobic seed particles and an aqueous dispersion comprising an emulsifier and an emulsion stabilizer and preparing a feedstock comprising encapsulated particles by homogenizing the emulsion, and forming a plurality of coated particles by spray drying the feedstock, wherein resulting particles comprises a porous shell disposed on or over a core and the core comprises at least one hydrophobic seed particle.

15 Claims, 6 Drawing Sheets

(51) Int. Cl.
*A61K 38/13* (2006.01)
*A61K 31/436* (2006.01)
*A61K 31/4704* (2006.01)
*A61K 31/365* (2006.01)
*A61K 45/06* (2006.01)
*B01J 2/04* (2006.01)

(52) U.S. Cl.
CPC .......... *A61K 31/365* (2013.01); *A61K 31/436* (2013.01); *A61K 31/4704* (2013.01); *A61K 38/13* (2013.01); *A61K 45/06* (2013.01); *B01J 2/04* (2013.01)

```
100
  ↓
110 — PREPARE AN OIL PHASE DISPERSION
      OF HYDROPHOBIC SEED PARTICLES
        ⇩
120 — PREPARE AN AQUEOUS SOLUTION CONTAINING
      AN EMULSIFIER AND AN EMULSION STABILIZER
        ⇩
130 — PREPARE AN EMULSION BY COMBINING THE OIL PHASE
      DISPERSION AND THE AQUEOUS SOLUTION
        ⇩
140 — PREPARE A FEEDSTOCK SOLUTION OF ENCAPSULATED
      PARTICLES BY HOMOGENIZING THE EMULSION
        ⇩
150 — SPRAY DRY THE FEEDSTOCK SOLUTION
      TO FORM COATED PARTICLES
```

FIG. 1

```
200
  ↓
210 — PREPARE AN AQUEOUS SOLUTION CONTAINING
      AN EMULSIFIER AND AN EMULSION STABILIZER
        ⇩
220 — PREPARE A FIRST EMULSION BY COMBINING
      THE AQUEOUS SOLUTION AND AN OIL MEDIA
        ⇩
230 — PREPARE A SECOND EMULSION
      BY HOMOGENIZING THE FIRST EMULSION
        ⇩
240 — PREPARE A FEEDSTOCK SOLUTION OF SUSPENDED PARTICLES
      BY COMBINING THE SECOND EMULSION AND
      HYDROPHOBIC SEED PARTICLES
        ⇩
250 — SPRAY DRY THE FEEDSTOCK SOLUTION
      TO FORM COATED PARTICLES
```

SPRAY-DRIED SOLID-IN-OIL-IN-WATER DISPERSIONS FOR INHALATION OF ACTIVE PHARMACEUTICAL INGREDIENTS

FIELD OF THE INVENTION

Embodiments of the invention relate to particulate agents and compositions comprising particulate agents for inhalation, and methods for preparing such particulate agents and compositions for inhalation, and well as therapeutic methods.

BACKGROUND TO THE INVENTION

Drug delivery methods and compositions that effectively provide the pharmaceutical compound at the specific site of action potentially serve to minimize toxic side effects, lower dosing requirements, and decrease therapeutic costs. The development of such systems for pulmonary drug delivery has long been a goal of the pharmaceutical industry.

Three common inhalation systems presently used to deliver drugs locally to the pulmonary air passages are dry powder inhalers (DPIs), metered dose inhalers (MDIs), and nebulizers. MDIs may be used to deliver medicaments in a solubilized form or as a dispersion. DPIs generally rely entirely on the patient's inspiratory efforts to introduce a medicament in a dry powder form to the lungs. Finally, nebulizers form a medicament aerosol to be inhaled by imparting energy to a liquid solution. While each of these methods and associated systems may prove effective in selected situations, inherent drawbacks, including formulation limitations, may limit usage.

Respiratory drug delivery places constraints on the drug particles contained within an inhaler. The drug particles generally must be in the respirable size range. A micronization process is often used in an effort to reach this size range. However, prior art powdered preparations for use in DPIs may fail to provide accurate, reproducible dosing over extended periods, in part because fine particles tend to aggregate over time, which disrupts the aerodynamic properties of the powder, thereby preventing large amounts of the aerosolized medicament from reaching the target area(s) of the lung.

One approach to overcoming this tendency toward aggregation is the use of large carrier particles (e.g. lactose) to prevent the fine drug particles from aggregating. However, substantial amounts of the drug fail to disengage from these large lactose particles and consequently deposit in the throat. As such, these carrier systems are relatively inefficient with respect to the fine particle fraction provided per actuation of the DPI.

Another solution to particle aggregation comprises making particles with relatively large geometric diameters (e.g., greater than 10 µm). Such large diameters reduce the amount and/or magnitude of particle interactions thereby preserving the flowability of the powder. The use of relatively large particles may result in dosing limitations when used in standard DPIs and provide for less than optimal dosing due to the potentially prolonged dissolution times. As such, there still remains a need for micro-sized particles that resist aggregation and preserve the flowability and dispersibility of the resulting powder.

Spray drying is an alternative manufacturing process for preparing powders for inhalation. Spray drying is a method for producing a dry powder from a liquid solution or a dispersion of particles in a liquid by drying with a hot gas. The resulting dry powders may be administered with either a DPI, or in suspension with a suitable propellant with a pMDI. Spray drying enables control of surface composition and particle morphology, factors critical in achieving good powder fluidization and dispersibility. This in turn leads to significant improvements in lung targeting and dose consistency relative to formulations based on blends of micronized API and coarse lactose monohydrate.

Forming stable suspensions of hydrophobic APIs (active pharmaceutical ingredient) in an aqueous phase can be challenging. Thermodynamically, the hydrophobic APIs want to remove contact with water. They do so by forming large flocs of drug particles. According to the literature, particle aggregation refers to formation of clusters in a colloidal suspension, and represents the most frequent mechanism leading to destabilization of colloidal systems. During this process, which normally occurs within short periods of time (seconds to hours), particles dispersed in the liquid phase stick to each other, and spontaneously form irregular particle clusters, flocs, or aggregates. This phenomenon is also referred to as coagulation or flocculation and such a suspension is also called unstable. Depending on the density of the particles and the density of the liquid medium, the particle flocs will either sediment or cream in the container. The poor stability of an aqueous-based feedstock comprising a hydrophobic drug leads to problems during spray-drying, as poor stability in the feedstock tank is reflected in variations in drug content over the batch.

Therefore, there is a need for micro-sized particulate agents (e.g., less than 10 µm) that resist aggregation and preserve the flowability and dispersibility of the resulting powder. There is also a need for methods for preparing such particulate agents. Additionally, there is a need for a process by which particles having a negligible or low solubility in water and/or particles having a lipophilic core can be prepared by spray drying a solid-in-oil emulsion.

SUMMARY OF THE INVENTION

It has been discovered that many hydrophobic drugs disperse effectively and form stable suspensions in liquid perfluorocarbons. This is surprising given the liquid perfluorocarbons generally exhibit "Teflon®-like" properties, where they are immiscible with both hydrophilic and lipophilic materials.

It has also been discovered that the suspensions of hydrophobic drug in liquid perfluorocarbon can be emulsified in water to form "stable" solid-in-oil-in-water (S-O-W) dispersions, where the dispersed oil droplets containing suspended drug particles are stabilized by long-chain phospholipids. When liquid phases are removed, such as by spray-drying, these dispersions form dry powder particles similar to those observed when the API particles are dispersed in the water phase, i.e., API particles coated with a porous layer of the excipients. Due to the improved stability of the drug suspensions, excellent content uniformity across the spray-dried batch is observed.

Embodiments of the invention accordingly comprise a composition of a plurality of particles, wherein substantially each particle comprises a porous shell disposed over a core of at least one hydrophobic seed particle comprising API within a fluorocarbon layer; and the porous shell comprises an emulsifier and an emulsion stabilizer. Note that the term shell is meant only to refer to relative positions of the components or layers, and does not connote or impute a measure of structural integrity.

Embodiments of the invention further comprise a composition of a plurality of particles, wherein the composition is adapted to be used in a variety of dry powder inhalers, such as passive or active, blister-based or capsule-based inhalers. In some embodiments the invention comprises a composition comprising a plurality of particles together with a passive inhaler device.

Embodiments of the invention comprise a process of dispersing hydrophobic "seed" particles of API within an oil medium, making an aqueous dispersion of an emulsifier and an emulsion stabilizer; combining the oil phase dispersion and the aqueous dispersion, and homogenizing the combination to produce a feedstock. Particulates are created by drying the feedstock, wherein each particle comprises a porous shell disposed over a core, and the core comprises at least one of the hydrophobic seed particles.

In some embodiments, processes, formulations and compositions of the present invention provide the benefit of high drug payload while maintaining good aerosol performance of the spray-dried powder. The S-O-W dispersions of the present invention allow each drug particle to be enclosed inside a thin layer of a fluorocarbon such as a perfluorocarbon, which is stabilized by a phospholipid/emulsion stabilizer layer in a aqueous medium. In this configuration, the surface of each drug particle is substantially coated with porous phospholipid after a drying process. Because of superior wetting property of the fluorocarbon, a minimal amount of fluorocarbon and phospholipid is required to create the S-O-W dispersions of the present invention.

In some embodiments, desirable seed particles have the properties of a narrow size distribution, substantially consist of only the API, and substantially retain the biochemical integrity and activity of the API. The particles provide a suitable solid to allow optional additional stabilization of the particles by coating or by microencapsulation.

Embodiments of the present invention comprise a method for forming particles, the method comprising: dispersing hydrophobic seed particles (for example API) within an oil medium to form a dispersion; preparing an aqueous dispersion comprising an emulsifier and an emulsion stabilizer; making a first, or coarse, emulsion by combining the oil phase dispersion and the aqueous dispersion under high-shear mixing, and then homogenizing to yield a second, or fine, emulsion to yield a feedstock comprising encapsulated hydrophobic seed particles wherein substantially all encapsulated particles comprise at least one of the hydrophobic seed particles, the oil medium, the emulsifier, and the emulsion stabilizer. The feedstock is then subject to a solvent removal process, such as spray-drying, to form a plurality of coated particles, wherein each coated particle comprises a porous shell disposed over a core, and wherein the core comprises at least one of the hydrophobic seed particles.

In other embodiments of the present invention there is a method for forming particles, wherein an aqueous dispersion comprising emulsifier and emulsion stabilizer is combined with an oil phase and subjected to high-shear mixing to yield the first, or coarse, emulsion. This coarse emulsion is then homogenized (such as by high-pressure homogenization) to yield a fine, or second emulsion, with discrete dispersions of the oil medium encapsulated by the emulsifier and the emulsion stabilizer. The second emulsion and hydrophobic seed particles are combined to form a feedstock, which is subject to a solvent removal process, wherein a plurality of coated particles are formed. Each coated particle comprises a porous shell disposed over a core, and the core comprises at least one of the hydrophobic seed particles.

Embodiments of the present invention comprise a feedstock, comprising: an aqueous solution comprising a plurality of suspended hydrophobic seed particles within a continuous phase of the aqueous solution; and dispersions within a discrete phase within the aqueous solution, wherein each dispersion comprises an oil medium encapsulated by an emulsifier and an emulsion stabilizer.

In some embodiments, a suspension-based process involves spray-drying a feedstock comprising a suspension of API particles dispersed in a continuous phase of an oil-in-water emulsion. The emulsion droplets may be stabilized by a monolayer of a long-chain phospholipid (e.g., DSPC) and calcium chloride. On drying the liquid phases evaporate and the resulting dry powder particles are comprised of the API particles coated with a porous layer of the excipients.

In some embodiments, the present invention comprises particles comprising a lipophilic active pharmaceutical ingredient (sometimes referred to herein as active agent) encompassed by an outer shell of phospholipid. Preferred APIs have a log P>0, often greater than 1, or greater than 3.

In some embodiments, a spray drying process of the feedstock comprises atomizing the feedstock to generate liquid droplets comprising a discrete phase of encapsulated particles within a continuous aqueous phase and forming the plurality of coated particles by drying the liquid droplets.

Embodiments of the invention relate to hydrophobic APIs which may comprise hydrophobic small molecules and/or hydrophobic peptides and/or proteins. The Table below lists exemplary proteins and peptides.

TABLE 1

| Antimicrobial peptides | | |
|---|---|---|
| Type | characteristic | Antimicrobial Peptides |
| Anionic peptides | rich in glutamic and aspartic acids | Maximin H5 from amphibians, Dermcidin from humans |
| Linear cationic α-helical peptides | lacking cysteine | Cecropins, andropin, moricin, ceratotoxin and melittin from insects, Magainin, dermaseptin, bombinin, brevinin-1, esculentins and buforin II from amphibians, CAP18 from rabbits, LL37 from humans |
| Catioinic peptide enriched for specific amino acid | rich in proline, arginine, phenylalanine, glycine, tryptophan | abaecin, apidaecins from honeybees, prophenin from pigs, indolicidin from cattle. |
| Anionic and cationic peptides that contain cysteine and form disulfide bonds | contain 1~3 disulfide bond | 1 bond: brevinins, 2 bonds: protegrin from pig, tachyplesins from horseshoe crabs, 3 bonds: defensins from humans, more than 3: drosomycin in fruit flies |

Other exemplary hydrophobic APIs comprise amyloid proteins including amyloid β-protein, Aβ-40, Aβ-42; immunosuppressive peptides; small molecules including: mycophenolate, cyclosporine, tacrolimus derivatives thereof, salts thereof, isomers thereof, mixtures thereof, or combinations thereof; hydrophobic surfactant proteins (e.g., SP-B, SP-C) and their biomimetics (e.g., KL4) or peptide analogues; hydrophobic peptides, hormones, and derivatives and mixtures of the foregoing.

In some embodiments, the hydrophobic seed particles comprise one or more beta-agonists, especially long-acting beta agonists, such as indacaterol one or more anti-muscarinic agents, such as mometasone; one or more mucociliary clearance agents, one or more sodium channel blockers, such as those of the class of achiral dimeric pyrazine derivatives; combinations thereof and mixtures thereof.

In some embodiments, the encapsulated particle comprises two or more of the hydrophobic seed particles within the dispersion encompassed by the outer shell. In some embodiments, the median particle diameter of the encapsulated particles is generally less than about 5 µm, such as from about 0.1 µm to about 7 µm, or about 0.5 µm to about 3.0 µm, or about 1.0 µm to about 2.0 µm. If multiple hydrophobic seed particles are contained within the core, the hydrophobic seed particles may have the same size and/or composition or the hydrophobic seed particles may have different sizes and/or compositions. The median particle diameter of the coated particles is generally less than about 5 µm.

In some embodiments, inhalable aerosol formulations comprising coated particles have improved properties, such as one or more of high payload, good emitted dose, reduced cohesive forces and good dispersiblity, over particles prepared by previous techniques, while maintaining good aerosol performance of spray-dried powder.

In some embodiments, a particulate composition comprises a plurality of coated particles containing an API, wherein each coated particle comprises a porous shell disposed on or over a core and the core comprises at least one hydrophobic seed particle comprising an agent/compound and generally comprises multiple hydrophobic seed particles. The porous shell comprises at least one emulsifier and at least one emulsion stabilizer.

BRIEF DESCRIPTION OF THE DRAWINGS

So that the manner in which the above recited features of embodiments of the invention can be understood in detail, a more particular description of the invention, briefly summarized above, may be had by reference to embodiments, some of which are illustrated in the appended drawings. It is to be noted, however, that the appended drawings illustrate only typical embodiments of the invention and are therefore not to be considered limiting of its scope, for the invention may admit to other equally effective embodiments.

FIG. 1 is a flow chart illustrating a method for forming coated particles, as described by embodiments herein.

FIG. 2 is a flow chart illustrating another method for forming coated particles, as described by other embodiments herein.

FIG. 5 is a graph illustrating the cumulative size distribution of the recovered aerosol fraction from a composition containing the coated particles formed in Example 3.

FIG. 6 depicts an SEM image of coated particles prepared by a spray drying process described in Example 4 and by embodiments disclosed herein.

DETAILED DESCRIPTION

Figure 3:
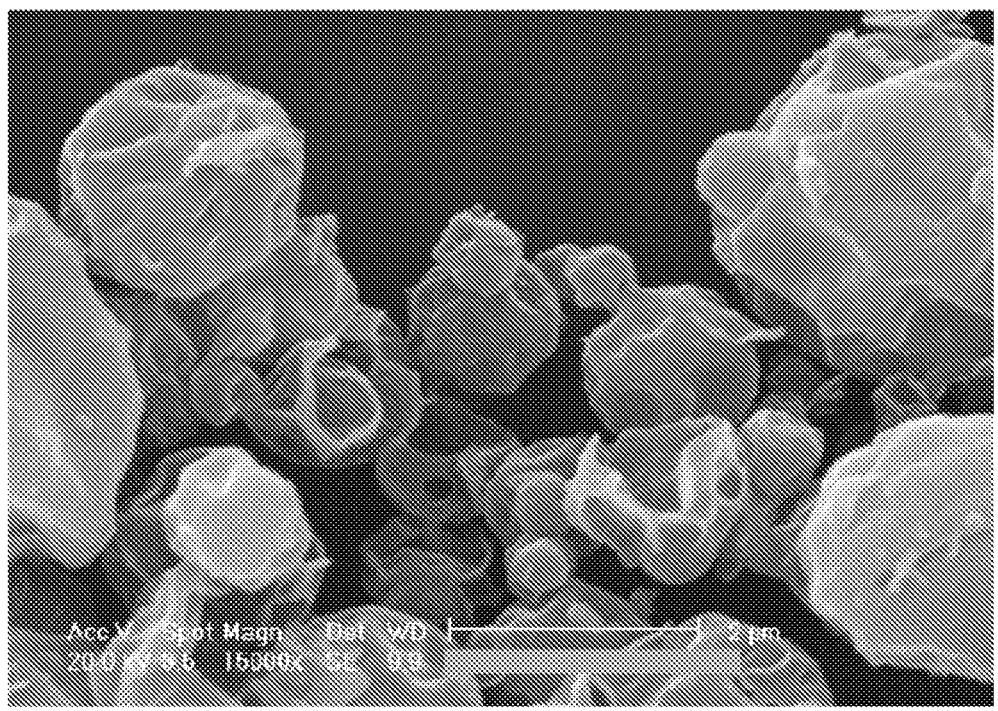
FIG. 3 depicts an SEM image of coated particles prepared by a spray drying process described in Example 3 and by embodiments disclosed herein.

Embodiments of the invention relate to particulate agents of active pharmaceutical ingredients or compounds, such as coated particles comprising active pharmaceutical ingredients, as well as to methods for preparing such particulate agents, formulations and compositions comprising the particulate agents, and inhalation devices comprising these particulate agents and formulations.

FIG. 1 is a flow chart illustrating a method, such as process 100, for forming coated particles and other particulate agents, as described by embodiments herein. Process 100 comprises preparing an oil phase dispersion of hydrophobic seed particles dispersed within an oil medium (step 110), preparing an aqueous dispersion comprising water, an emulsifier, and an emulsion stabilizer (step 120), and preparing an emulsion by combining the oil phase dispersion and the aqueous dispersion (step 130). Process 100 also comprises preparing a feedstock of encapsulated particles by homogenizing the emulsion using a high-pressure homogenization process (step 140).

The final feedstock comprising the encapsulated particles is a solid-in-oil-in-water (S-O-W) dispersion, in which the hydrophobic seed particles are encapsulated in a droplet of the oil medium and the outer surface of the droplet—the oil phase—is stabilized by the emulsifier and the emulsion stabilizer. Process 100 further comprises spray drying the feedstock to produce a plurality of coated particles (step 150). Each coated particle comprises a porous shell disposed on or over a core and the core comprises one or multiple hydrophobic seed particles.

Steps 110 and 120 may be practiced in any order, as long as the oil phase dispersion of hydrophobic seed particles of step 110 and the aqueous dispersion comprising the emulsifier and the emulsion stabilizer of step 120 are prepared prior to preparing the emulsion during in 130. Therefore, in various embodiments, step 110 may be started or completed prior to, during, or subsequent to step 120.

Steps 110-140 of process 100 are utilized to prepare a particulate feedstock which comprises an aqueous dispersion comprising a plurality of encapsulated particles in some embodiments. The encapsulated particles form a discrete phase within a continuous phase of the aqueous solution and substantially all encapsulated particles comprise a dispersion encompassed by an outer shell. The dispersion may comprise at least one of the hydrophobic seed particles and the oil medium. The outer shell generally comprises the emulsifier and the emulsion stabilizer. In many embodiments, substantially all of the encapsulated particles comprise two or more of the hydrophobic seed particles within the dispersion encompassed by the outer shell.

Steps 110-150 of process 100 are utilized to prepare a particulate composition comprising a plurality of coated particles in some embodiments. Each of the coated particles comprises a porous shell disposed over and around a core. The porous shell comprises an emulsifier and an emulsion stabilizer. The core comprises at least one hydrophobic seed particle and generally comprises multiple hydrophobic seed particles. In some embodiments, the hydrophobic seed particles comprise an immunosuppressive agent/compound, or a long-acting beta agonist or an epithelial sodium channel blocker, or combinations thereof.

Step 110 of process 100 comprises preparing an oil-phase dispersion of hydrophobic seed particles dispersed within an oil medium, such as a fluorocarbon, or perfluorocarbon (e.g., PFOB). In some embodiments, the oil-phase dispersion has a concentration of hydrophobic seed particles within a range from about 0.05 g/mL to about 0.5 g/mL, for example, about 0.1 to 0.3 g/mL. The oil-phase dispersion is prepared by combining hydrophobic seed particles and the oil medium. In some embodiments, the oil phase dispersion is prepared by combining hydrophobic seed particles of a mass within a range from about 5 g to about 15 g, for example, about 10 g and the oil medium of a volume within a range from about 30 mL to about 100 mL, for example, about 50 mL.

A shear mixer, such as a high-shear mechanical mixer, may be used to mix, stir, or otherwise combine the hydrophobic seed particles and the oil medium while forming the oil-phase dispersion. An exemplary high-shear mechanical mixer useful for mixing in any applicable steps requiring or benefiting from high shear, such as any or all of steps 110, 220 and 230 is commercially available as the ULTRA-TURRAX® model T-25 mixer. The oil medium and the hydrophobic seed particles within the mixture are generally stirred, mixed, or otherwise combined by the high-shear mixer at a rate within a range from about 6,000 rpm to about 10,000 rpm, such as about 8,000 rpm, for a time period within a range from about 5 minutes to about 10 minutes while forming the oil-phase dispersion. The oil-phase dispersion comprises the hydrophobic seed particles substantially dispersed within the oil medium.

The hydrophobic seed particles comprise at least one compound/agent, but may comprise two or more compounds/agents. Additionally or alternately, a plurality of hydrophobic seed particles may comprise a mixture of different particles varying in composition of concentration of API and/or non-active agents. The hydrophobic seed particles may comprise active and non-active compounds, pharmaceutical ingredients, and/or agents. In some embodiments described herein, the hydrophobic seed particles comprise at least one active pharmaceutical ingredient (API).

In some embodiments, the hydrophobic seed particles comprise at least one or more long-acting beta agonists. In some embodiments, the hydrophobic seed particles comprise at least one or more epithelial sodium channel blockers. The hydrophobic seed particles are generally insoluble or substantially insoluble in the oil medium and/or water under the temperature and pressure conditions described herein. In some embodiments, the hydrophobic seed particles comprise at least one or more immunosuppressive agents/compounds.

The hydrophobic seed particles are generally prepared by a process or technique which comprises spray drying, supercritical spray drying, solution enhanced dispersion, dry milling (e.g., jet milling), wet milling (e.g., ball milling), cryogenic milling, crystallization techniques, precipitation techniques, or combinations thereof. The hydrophobic seed particles generally have a median particle diameter of less than about 20 μm, such as less than about 10 μm. In many embodiments, the hydrophobic seed particles generally have a medium particle diameter within a range from about 0.1 μm to about 8.0 μm, such as from about 0.2 μm to about 6.0 μm, such as from about 0.5 μm to about 5.0 μm, such as from about 0.5 μm to about 3.0 μm, such as from about 1.0 μm to about 2.0 μm.

If micronized, the drug particles may be prepared by either top-down or bottom-up manufacturing processes. Top-down manufacturing processes include jet milling, ball milling, medium milling, and high pressure homogenization. Bottom-up processes include: spray-drying, spray freeze-drying, supercritical fluid technologies (rapid expansion and anti-solvent), templating and microfabrication, lithography, and other particle precipitation techniques (e.g., spinodal decomposition), for example in the presence of ultrasonic energy to ensure crystallization of the drug. Note that the term micronized is intended to encompass any and all processes, whether physical, chemical, mechanical or otherwise, for providing a sufficiently sized and/or shaped drug particle.

The oil medium is generally a carbon based oil or solvent which comprises perfluorocarbons (PFCs), hydrofluorocarbons (HFCs), hydrocarbons (HCs), and other oils or solvents. In many embodiments, the oil medium comprises a perfluorocarbon medium that comprises perfluorocarbon compounds. Exemplary perfluorocarbon compounds include perfluorooctyl bromide, perfluorobutane, perfluorooctane, perfluoroheptane, perfluorohexyl bromide, perfluorohexane, perfluoropentane, perfluorobutyl bromide perfluorodecalin, perfluorooctyl ethane (PFOE), perfluorohexyl butane, derivatives thereof, mixtures thereof, or combinations thereof. In some embodiments, the perfluorocarbon is Fluorinert™ a proprietary family of fluorinated liquids available for the 3M Company, St Paul, Minn., USA. In many embodiments, the oil medium is a perfluorocarbon medium, such as perfluorooctyl bromide (PFOB or perflubron). In many embodiments, the oil medium may be an oil media, i.e. a mixture or combination. The term medium is used herein to refer to a singular oil or combination thereof.

Step 120 of process 100 comprises preparing an aqueous dispersion that comprises an emulsifier and an emulsion stabilizer. At least one emulsifier, at least one emulsion stabilizer, and water are combined and mixed to comprise the aqueous dispersion. Additional compounds, such as excipients may also be included in the aqueous dispersion. In one embodiment, the aqueous dispersion comprises distearoylphosphatidylcholine (DSPC) as the emulsifier and calcium chloride ($CaCl_2$) as the emulsion stabilizer. The water may be deionized water or distilled water. Alternatively, the water may be substituted with an aqueous liquid that comprises other compounds/agents in water, such as organic solvents (e.g., ethanol, tetrahydrofuran), surfactants, salts, and/or other compounds.

In some embodiments, the aqueous dispersion has a concentration of the emulsifier within a range from about 3 mg/mL to about 30 mg/mL, for example, about 12 mg/mL and a concentration of the emulsion stabilizer within a range from about 3 mg/mL to about 12 mg/mL, for example, about 9 mg/mL. The aqueous dispersion may be prepared by combining the emulsifier of a mass within a range from about 2 g to about 8 g, for example, about 5 g, the emulsion stabilizer of a mass within a range from about 200 mg to about 800 mg, for example, about 450 mg, and water of a volume within a range from about 300 mL to about 600 mL, for example, about 450 mL. In some embodiments, a percentage of emulsifier is about 0.002 to 0.02, a percentage of emulsion stabilizer is about 0.0002 to 0.002, and the remainder is water.

In some embodiments, the emulsifier and/or the emulsion stabilizer is added to the water. The water is generally heated and maintained at a temperature above the gel-to-liquid-crystal phase transition of the emulsifier, typically within a range from about 40° C. to about 100° C., such as from about 60° C. to about 90° C., such as from about 70° C. to about 80° C., for example, about 75° C. while forming the aqueous dispersion during step 120.

The emulsifier generally comprises a lipid from natural and/or synthetic sources. The emulsifier is used in varying concentrations to form a structural matrix. Generally compatible lipids have a gel-to-liquid-crystal phase transition greater than about 40° C. Many useful lipids have a relatively long carbon chain (e.g., $C_{16}$-$C_{22}$) and are saturated lipids. In many embodiments, the emulsifying lipid comprises a phospholipid compound. Several exemplary phospholipid compounds useful as the emulsifier include distearoylphosphatidylcholine (DSPC), dimyristoylphosphatidylcholine (DMPC), diarachidoylphosphatidylcholine (DAPC), dipalmitoylphosphatidylcholine (DPPC), dilauroylphosphatidylcholine (DLPC), dioleoylphosphatidylcholine (DOPC), dibehenoylphosphatidylcholine (DBPC), derivatives thereof, mixtures thereof, or combinations thereof. In many embodiments, the emulsifier comprises DSPC. Preferably, the acyl chains of the phospholipids should be saturated so that the gel-liquid crystal phase transition of the phospholipid is greater than 0° C., such as greater than 40° C. or 50° C.

The emulsion stabilizer generally comprises at least one emulsion stabilizing compound or excipient. Exemplary emulsion stabilizers include inorganic salts, organic salts, carbohydrates, amino acids, derivatives thereof, mixtures thereof, or combinations thereof. In some embodiments, the emulsion stabilizer comprises an inorganic salt, an organic salt, or combinations thereof. Exemplary emulsion stabilizing compounds or excipients utilized as the emulsion stabilizer include calcium chloride, calcium citrate, calcium ascorbate, sodium chloride, sodium phosphate, sodium citrate, sodium ascorbate, derivatives thereof, mixtures thereof, or combinations thereof. In some embodiments, the emulsion stabilizer comprises calcium chloride.

Step 130 of process 100 comprises preparing an emulsion by combining and mixing the oil phase dispersion prepared in step 110 and the aqueous dispersion prepared in step 120. Generally, the oil phase dispersion comprising the hydrophobic seed particles is added into aqueous dispersion containing emulsifier and stabilizer under high-shear mixing to form an emulsion. The prepared emulsion is generally coarse (relative to the final feedstock prepared in step 140) and is an S-O-W dispersion—in which at least one solid hydrophobic seed particle is encapsulated in a droplet of the oil medium and the outer surface of the droplet—the oil phase—is stabilized by the emulsifier and the emulsion stabilizer.

The emulsion in step 130 may be prepared by combining the oil phase dispersion of a mass within a range from about 20 g to about 120 g, for example, about 60 g, and the aqueous dispersion of a mass within a range from about 300 g to about 600 g, for example, about 450 g.

A shear mixer, such as a high-shear mechanical mixer, may be used to mix, stir, or otherwise combine the oil phase dispersion and the aqueous dispersion while forming this emulsion.

Step 140 of process 100 comprises preparing a feedstock of encapsulated particles by homogenizing the coarse emulsion prepared in step 130 during a homogenization process to form the fine emulsion of the feedstock. The final feedstock comprising the encapsulated particles is also an S-O-W dispersion, in which the hydrophobic seed particles are encapsulated in a droplet of the oil medium and the outer surface of the droplet—the oil phase—is stabilized by the emulsifier and the emulsion stabilizer. Therefore, each encapsulated particle comprises a dispersion encompassed by an outer shell, the dispersion comprises at least one of the hydrophobic seed particles and the oil medium, and the outer shell comprises the emulsifier and the emulsion stabilizer. In many embodiments, substantially all of the encapsulated particles comprise two or more of the hydrophobic seed particles within the dispersion encompassed by the outer shell.

A homogenizer, such as a high-pressure homogenizer, may be used to further mix, stir, combine, or otherwise homogenize the coarse emulsion to form the fine emulsion for use as a feedstock. An exemplary high-pressure homogenizer useful for homogenizing in step 140 is commercially available as the AVESTIN® model C-50 homogenizer. During the homogenization process, the coarse emulsion is homogenized or otherwise processed in the homogenizer maintained at a pressure within a range from about 10,000 psi (pounds per square inch) to about 20,000 psi, for example, about 15,000 psi and a temperature within a range from about 5° C. to about 25° C., for example, about 15° C. The coarser emulsion is passed once or multiple times (e.g., about 2-10 passes) through the homogenizer to prepare a finer emulsion as the feedstock.

In some embodiments, the feedstock prepared in step 140 is a fine S-O-W dispersion and comprises hydrophobic seed particles of an API/compound which are encapsulated in droplets of an oil medium and the outer surface of the droplet—the oil phase—is stabilized by an emulsifier and the emulsion stabilizer. In more specific embodiments, the feedstock prepared in step 140 is a fine S-O-W dispersion and comprises hydrophobic seed particles of an API/compound (e.g., cyclosporine or indacaterol) which are encapsulated in droplets of the oil medium comprising a hydrofluorocarbon (e.g., PFOB) and the outer surface of the droplet is stabilized by an emulsifier (e.g., DSPC) and emulsion stabilizer (e.g., $CaCl_2$).

Embodiments of the present invention provide several advantages over previous techniques. The hydrophobic seed particles comprising lipophilic drug compounds/pharmaceutical ingredients are encapsulated inside the droplets of the oil medium, which prevents the aggregation of particles in the aqueous system. Generally, lipophilic/hydrophobic materials in a hydrophilic/aqueous system tend to form aggregates to reduce their Gibbs free energy. Also, the physical stability of the S-O-W dispersion of the feedstock has been demonstrated by measuring the size of droplets, which does not change or substantially change over a two-week period in many embodiments. The distinctive configuration of the encapsulated particles of the S-O-W dispersion serves as a template during drying.

The encapsulated particles within the feedstock generally have a median particle diameter or a mean particle size of less than about 20 μm, such as about 10 μm or less, such as within a range from about 0.1 μm to about 10 μm, such as from about 0.5 μm to about 10 μm, such as from about 0.8 μm to about 8.0 μm, such as from about 1.0 μm to about 5.0 μm, such as from about 2.0 μm to about 3.0 μm. An outer layer of the encapsulated particles within the feedstock generally has an average thickness of less than about 10 μm, such as less than about 5 μm, such as less than about 4 μm, such as less than about 2 μm. In some embodiments, the outer layer generally has an average thickness within a range from about 0.1 μm to about 1.5 μm, such as from about 0.2

μm to about 1.0 μm, such as from about 0.3 μm to about 0.7 μm, such as from about 0.4 μm to about 0.6 μm, for example, about 0.5 μm. In many embodiments, the encapsulated particles have a median particle diameter within a range from about 2 μm to about 3 μm, an average thickness of the outer layer within a range from about 0.4 μm to about 0.6 μm, and comprise hydrophobic seed particles that have a diameter within a range from about 1 μm to about 2 μm.

Step 150 of process 100 comprises spray drying the feedstock to produce a plurality of coated particles, such that each coated particle substantially comprises a porous shell disposed on or over a core. The core may be a single hydrophobic seed particle or may comprise multiple hydrophobic seed particles. The spray drying process results in a distribution of spray dried particles, each of which comprises one or several seed particles, and each seed particle is in a core/shell configuration. Each of the solid cores, comprising one or multiple hydrophobic seed particles, is coated with a porous shell comprising a mixture of at least one emulsifier and at least one emulsion stabilizer (e.g., a mixture of DSPC/CaCl$_2$).

The coated dried particles formed by process 100 generally have a median particle diameter—also known as a median particle size—of less than about 20 μm, such as about 15 μm or less, such as about 10 μm or less. In some embodiments, the median particle diameter of the coated particles is generally within a range from about 0.1 μm to about 8.0 μm, such as from about 0.5 μm to about 8.0 μm, such as from about 1.0 μm to about 5.0 μm, such as from about 1.0 μm to about 3.0 μm, such as from about 1.5 μm to about 2.5 μm, for example, about 2.0 μm. In many embodiments, the median particle diameter of the coated particles is within a range from about 0.5 μm to about 8.0 μm, such as from about 1.0 μm to about 5.0 μm. In some embodiments, the median particle diameter of the coated particles is within a range from about 2.0 μm to about 4.0 μm, such as from about 2.5 μm to about 3.5 μm. In other embodiments, the median particle diameter of the coated particles is within a range from about 1.0 μm to about 3.0 μm, such as from about 1.5 μm to about 2.5 μm, for example, about 2.0 μm. The average thickness of the porous shell on or over the core of the coated particle is generally less than about 5 μm, such as within a range from about 0.1 μm to about 1.5 μm, or from about 0.2 μm to about 1.0 μm.

In embodiments of the present invention, emitted aerosol formulations comprising coated particles have improved properties over formulations that comprise particles prepared by previous techniques. In some embodiments, an aerosol formulation comprising coated particles has a mean emitted dose of at least 85% or greater, such as 90% or greater, such as 95% or greater, such as 97% or greater, such as 99% or greater. In one embodiment, the aerosol formulation comprising coated particles has a mean emitted dose of about 87%. In another embodiment, the aerosol formulation comprising coated particles has a mean emitted dose of about 95%. The emitted aerosol particles comprising the coated particles generally have a mass median aerodynamic diameter (MMAD) of generally less than about 30 μm, such as about 20 μm or less, such as about 10 μm or less. In some embodiments, the MMAD of the aerosol particles is within a range from about 0.5 μm to about 8.0 μm, and more narrowly within a range from about 1.0 μm to about 5.0 μm, for example, about 2.0 μm or about 3.5 μm.

FIG. 2 is a flow chart illustrating another method for forming coated particles and other particulate agents, as described by other embodiments herein. Process 200 comprises preparing an aqueous dispersion comprising an emulsifier and an emulsion stabilizer (step 210), preparing a first or course emulsion by combining the aqueous dispersion and an oil medium (step 220), and preparing (step 230) a second or fine emulsion by homogenizing the first emulsion (such as by a high-pressure homogenization process). Process 200 further comprises preparing a feedstock of suspended particles by combining the second emulsion and the hydrophobic seed particles (step 240). The feedstock comprises a continuous aqueous phase with suspended particles and a second discrete phase of the fine second emulsion which are stabilized by at least one emulsifier (e.g., DSPC) and/or at least one emulsion stabilizer (e.g., $CaCl_2$). Process 200 further comprises spray drying the feedstock to produce a plurality of coated particles (step 250). Each of the coated particles comprises a porous shell disposed on or over a core and the core comprises at least one of the hydrophobic seed particles.

Steps 210-240 of process 200 may be utilized to prepare a particulate feedstock which comprises a plurality of suspended particles and discrete dispersion phases of the second emulsion within the aqueous phase.

Steps 210-250 of process 200 may be utilized to prepare a particulate composition comprising a plurality of coated particles. Each of the coated particles comprises a porous shell disposed over and around a core. The porous shell comprises an emulsifier and an emulsion stabilizer. The core comprises at least one hydrophobic seed particle and generally comprises multiple hydrophobic seed particles.

Step 210 of process 200 comprises preparing an aqueous dispersion that comprises an emulsifier and an emulsion stabilizer. The solution may be prepared as described herein and in particular, with reference to step 120.

Step 220 of process 200 comprises preparing a coarse, or first, emulsion by combining and mixing the aqueous dispersion prepared in step 210 and an oil medium (e.g., PFOB). In many embodiments, the aqueous dispersion comprising the emulsifier and the emulsion stabilizer is rapidly stirred by high-shear mixing while the oil medium is added to the aqueous dispersion forming the coarse, or first, emulsion. The prepared first emulsion is coarse (relative to the fine, or second emulsion prepared in step 230) and has an interface between the oil medium and the aqueous dispersion. The interface is stabilized by the emulsifier and the emulsion stabilizer (e.g., DSPC and $CaCl_2$).

The coarse or first emulsion is prepared in step 220 by combining the aqueous dispersion and the oil medium in a ratio of about 5:1 to 1:5, such as 1:1. The emulsion may be prepared as described herein and in particular, with reference to step 120.

Step 230 of process 200 comprises preparing a fine, or second, emulsion by homogenizing the coarse, or first emulsion prepared in step 220 during a homogenization process. The first emulsion is generally coarser than the second emulsion. A homogenizer, such as a high-pressure homogenizer, may be used to further mix, stir, combine, or otherwise homogenize the coarse first emulsion while preparing the fine second emulsion. An exemplary high-pressure homogenizer useful for homogenizing in step 230 is commercially available as the AVESTIN® model C-50 homogenizer. Homogenization is carried out as described herein, and with particular reference to process 100 and/or step 140.

A shear mixer, such as a high-shear mechanical mixer, may be used to mix, stir, or otherwise combine the hydrophobic seed particles and the second emulsion. The shear mixer may be as described herein and in particular, with reference to process 100 and/or steps 110 and/or 130.

The hydrophobic seed particles comprise at least one compound/agent, but may comprise two or more compounds/agents. Alternately, a plurality of hydrophobic seed particles may comprise a mixture of different particles varying in composition of concentration of API and/or non-active agents. The hydrophobic seed particles may comprise active and non-active compounds, substances, and/or agents. In many embodiments described herein, the hydrophobic seed particles comprise at least one API, for example, one or more immunosuppressive agents/compounds, one or more beta-agonists one or more sodium channel blockers and mixtures thereof. The hydrophobic seed particles are generally insoluble or substantially insoluble in the oil medium and/or water under the temperature and pressure conditions described herein.

The hydrophobic seed particles are prepared by a process, method or technique, and have characteristics as described herein and with particular reference to process 100.

Step 240 of process 200 comprises preparing a feedstock of suspended particles by combining and mixing the fine second emulsion prepared in step 230 and the hydrophobic seed particles. The final feedstock comprises the suspended particles as well as a second discrete phase comprising the emulsifier, the emulsion stabilizer, and the oil medium.

The feedstock of suspended particles may be prepared in step 240 by combining the fine, or second emulsion with the aqueous suspension in a ratio (emulsion:aqueous suspension) of about 4:1 to 1:5, such as about 3:1 to 1:1.

A shear mixer, such as that described in process 100, may be used to mix, stir, or otherwise combine the fine second emulsion and the hydrophobic seed particles while preparing the feedstock.

In some embodiments, the feedstock prepared in step 240 comprises suspended hydrophobic seed particles of an active agent/compound as well as dispersions or suspended droplets of the oil medium comprising a hydrofluorocarbon (e.g., PFOB) encapsulated and stabilized by an outer surface of the emulsifier (e.g., DSPC) and the emulsion stabilizer (e.g., $CaCl_2$).

Step 250 of process 200 comprises spray drying the feedstock to produce a plurality of coated particles, such that each coated particle comprises a porous shell disposed on or over a core. The core may be a single hydrophobic seed particle or may comprise multiple hydrophobic seed particles. Each of the solid cores, comprising one or multiple hydrophobic seed particles, is coated with a porous shell comprising a mixture of at least one emulsifier and at least one emulsion stabilizer (e.g., a mixture of DSPC/$CaCl_2$).

The feedstock prepared in step 240 generally comprises a solution, a course suspension, a slurry, a colloidal dispersion, or combinations thereof that may be atomized using the selected spray-drying apparatus. In some embodiments, the feedstock may comprise a colloidal system such as an emulsion, reverse emulsion, microemulsion, multiple emulsion, particulate dispersion, slurry, or combinations thereof. Typically, the feedstock is sprayed into a current of warm filtered air or another gaseous environment that evaporates the solvent and conveys the dried product to a collector. The spent air, water vapor, and/or other gas may then be exhausted with any other solvent or by-products. A spray drying apparatus, such as a spray dryer, may be used to spray dry the feedstock while preparing the plurality of coated particles. An exemplary spray drying apparatus useful for spray-drying the feedstock in step 260 while preparing the coated particles is a BUCHI® mini spray-drier, commercially available from BUCHI Labortechnik AG, of Switzerland. Other exemplary spray drying apparatus are commercially available, such as from the DEA Niro Company of Denmark.

In an embodiment, the porous shell—comprising at least one emulsifier and at least one emulsion stabilizer/excipient—is disposed on or over the core of each coated particle formed by process 200. The core may comprise a single hydrophobic seed particle, but in some embodiments, comprises multiple hydrophobic seed particles, such as two or more of the hydrophobic seed particles. If multiple hydrophobic seed particles are contained within the core, the hydrophobic seed particles may have the same size and/or composition or the hydrophobic seed particles may have different sizes and/or compositions.

The coated particles formed by process 200 possess generally the same physical characteristics (such as median particle diameter size and distribution, and shell thickness) as those formed by the process 100.

In many of the embodiments described herein, the spray drying parameters may be adjusted, controlled, and/or maintained to help provide the desired particle size and to result in a product (e.g., coated particles) of the desired properties and activity of the medicament. The inlet and outlet temperatures may be adjusted depending on the melting temperature, decomposition temperature, or other properties of the formulation components and the composition of the feedstock.

In some embodiments, the spray drying process of the feedstock comprises atomizing the feedstock to generate liquid droplets comprising a discrete phase of encapsulated particles within a continuous aqueous phase and forming the plurality of coated particles by drying the liquid droplets. The spray drying process comprises forming the coated particles and water vapor by drying the liquid droplets at a first or inlet temperature within a drying chamber, such as at the inlet temperature of the spray drying chamber. Thereafter, the spray drying process generally comprises flowing the coated particles and the water vapor from the drying chamber to a collection chamber at a second or outlet temperature, and separating the coated particles from the water vapor by a centrifugal process within the collection chamber. Subsequently the spray drying process of the feedstock further comprises, in embodiments herein, collecting the coated particles in a collection vessel maintained at a third or collection temperature within the collection chamber.

An "active pharmaceutical ingredient" as described herein may be a substance capable of performing some useful function in an end product, such as a pharmacophore. The active pharmaceutical ingredient may comprise a single pharmaceutical ingredient or a mixture of two or more. The active pharmaceutical ingredient may comprise a monomeric, oligomeric or polymeric, organic (including organometallic) or inorganic, hydrophilic or hydrophobic, polar or non-polar. In some embodiments, the active pharmaceutical ingredient comprises a small molecule or a macromolecule such as a protein or peptide (including enzymes, hormones, antibodies and antigens), nucleotide, nucleoside, or nucleic acid. Other potential active pharmaceutical ingredients include vitamins, amino acids, lipids, and carbohydrates.

In many embodiments, the active pharmaceutical ingredient comprises a pharmaceutically or active ingredient, excipient, or a mixture of two or more thereof. The active pharmaceutical ingredient may comprise one which is suitable for delivery by inhalation (which term includes nasal and/or oral inhalation), whether for local administration or for systemic delivery via the lungs.

In many embodiments, the active pharmaceutical ingredient or the particles of the active pharmaceutical ingredient may comprise one or more hydrophobic compounds, such as hydrophobic seed particles. In some embodiments, the active pharmaceutical ingredient or the particles of the active pharmaceutical ingredient may comprise one or more immunosuppressive agents/compounds (e.g., cyclosporine, tacrolimus, or mycophenolate). In some embodiments, the API can comprise any active pharmaceutical ingredients that are useful for treating obstructive or inflammatory airways diseases, particularly asthma and COPD. Suitable active ingredients include long acting β2-agonists such as salmeterol, formoterol, indacaterol and salts thereof, muscarinic antagonists such as tiotropium and glycopyrronium and salts thereof, and corticosteroids including budesonide, ciclesonide, fluticasone and mometasone and salts thereof. Suitable exemplary combinations include (indacaterol maleate and glycopyrronium bromide), (indacaterol acetate and glycopyrronium bromide), (indacaterol xinafoate and glycopyrronium bromide), (indacaterol maleate and mometasone furoate), (formoterol fumarate and budesonide), (salmeterol xinafoate and fluticasone propionate), (salmeterol xinafoate and tiotropium bromide), (formoterol fumarate and tiotropium bromide), (indacaterol maleate, mometasone furoate and glycopyrronium bromide), (indacaterol acetate and mometasone furoate), (indacaterol xinafoate, mometasone furoate and glycopyrronium bromide), (formoterol fumarate, fluticasone propionate and tiotropium bromide), (fluticasone propionate and indacaterol), (fluticasone propionate and glycopyrronium bromide), as well as combinations of the foregoing.

Exemplary biologically APIs are meant to encompass, where applicable, analogues, agonists, antagonists, inhibitors, isomers, and pharmaceutically acceptable salt forms thereof. In reference to peptides and proteins, some embodiments encompass synthetic, recombinant, native, glycosylated, non-glycosylated, and biologically active fragments and analogs thereof.

With regard to pharmaceutical preparations, any bioactive agent that may be formulated in the disclosed hydrophobic seed particles, insoluble seed particles, or the coated particles is expressly held to be within the scope of embodiments of the invention including utilized during processes 100 and 200 described herein. In many embodiments, the selected bioactive agent may be administered in the form of an aerosolized medicament. Accordingly, particularly compatible bioactive agents include any drug that may be formulated as a flowable dry powder or which is relatively insoluble in selected dispersion medium. In addition, in many embodiments the formulated agents are subject to pulmonary or nasal uptake in physiologically effective amounts. Compatible bioactive agents include hydrophilic and lipophilic respiratory agents, pulmonary surfactants, bronchodilators, antibiotics, antivirals, anti-inflammatories, steroids, antihistaminics, leukotriene inhibitors or antagonists, anticholinergics, antineoplastics, anesthetics, enzymes, cardiovascular agents, genetic material including DNA and RNA, viral vectors, immunoactive agents, imaging agents, vaccines, immunosuppressive agents, peptides, proteins, derivatives thereof, or combinations thereof. In many embodiments, the bioactive agents for inhalation therapy include mast cell inhibitors (anti-allergics), bronchodilators, and anti-inflammatory steroids such as, for example, cromoglycate (e.g., the sodium salt), and albuterol (e.g., the sulfate salt). In many embodiments, aerosolized immunosuppressive agents include cyclosporine, tacrolimus, or mycophenolate.

More specifically, exemplary medicaments or bioactive agents utilized within the hydrophobic seed particles, insoluble seed particles, or the coated particles during processes 100 and 200 described herein may be selected from, for example, analgesics, e.g., codeine, dihydromorphine, ergotamine, fentanyl, or morphine; anginal preparations, e.g., diltiazem; mast cell inhibitors, e.g., cromolyn sodium; antiinfectives, e.g., cephalosporins, macrolides, quinolines, penicillins, streptomycin, sulphonarnides, tetracyclines and pentamidine; antihistamines, e.g., methapyrilene; anti-inflammatories, e.g., fluticasone propionate, beclomethasone dipropionate, flunisolide, budesonide, tripedane, cortisone, prednisone, prednisilone, dexamethasone, betamethasone, or triamcinolone acetonide; antitussives, e.g., noscapine; bronchodilators, e.g., ephedrine, adrenaline, fenoterol, formoterol, isoprenaline, metaproterenol, salbutamol, albuterol, salmeterol, terbutaline; diuretics, e.g., amniloride; anticholinergics, e.g., ipatropium, atropine, or oxitropium; lung surfactants (e.g., SURFAXIN® surfactant or lucinactant, EXOSURF® surfactant, SURVANTA® surfactant or beractant); xanthines, e.g., aminophylline, theophylline, caffeine; therapeutic proteins and peptides, e.g., DNAse, insulin, glucagon, LHRH, nafarelin, goserelin, leuprolide, interferon, rhu IL-1 receptor, macrophage activation factors such as lymphokines and muramyl dipeptides, opioid peptides and neuropeptides such as enkaphalins, endophins, renin inhibitors, cholecystokinins, DNAse, growth hormones, leukotriene inhibitors and the like. In addition, bioactive agents that comprise an RNA or DNA sequence, particularly those useful for gene therapy, genetic vaccination, genetic tolerization or antisense applications, may be incorporated in the disclosed dispersions as described herein.

One specific class of hydrophobic seed particle comprising an API is the class of sodium channel blockers, such as epithelial sodium channel blockers. An exemplary epithelial sodium channel blocker is an achiral dimeric pyrazine derivative having the chemical name of: [4-(4-[N'(3,5-Diamino-6-chloro-pyrazine-2-carbonyl)-guanidino]-piperidine-1-carbonyl)-phenyl]-(4-[N'(3,5-Diamino-6-chloro-pyrazine-2-carbonyl)-guanidino]-piperidine-1-yl)-methanone. This compound is more fully described in U.S. Pat. No. 8,318,935, the disclosure of which is incorporated by reference herein.

A specific class of hydrophobic seed particle comprising an API is the class of beta-agonists, such as long acting beta-agonists. An exemplary long-acting beta-agonist is indacaterol (i.e. (R)-5-[2-(5,6-diethyl-indan-2-ylamino)-1-hydroxyethyl]-8-hydroxy-1H-quinolin-2-one) or a salt thereof. This is a β2-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts.

In some embodiments an API may comprise mometasone (i.e. (11β, 16α)-9,21-dichloro-17-[(2-furanylcarbonyl)oxy]-11-hydroxy-16-methylpregna-1, 4-diene-3,20-dione, alternatively designated 9,21-dichloro-16-methyl-1,4-pregnadiene-11β,17α-diol-3,20-dione 17-(2'-furoate)) or a derivative thereof, for example mometasone furoate and mometasone furoate monohydrate. Mometasone furoate and its preparation are described in U.S. Pat. No. 4,472,393. It use in the treatment of asthma is described in U.S. Pat. No. 5,889,015. It use in the treatment of other respiratory diseases is described in U.S. Pat. Nos. 5,889,015, 6,057,307, 6,057,581, 6,677,322, 6,677,323 and 6,365,581.

Suitable inhalers include dry powder inhaler (DPIs). Some such inhalers include unit dose inhalers, where the dry powder is stored in a capsule or blister, and the patient loads one or more of the capsules or blisters into the device prior to use. Other multi-dose dry powder inhalers include those where the dose is pre-packaged in foil-foil blisters, for example in a cartridge, strip or wheel.

Preferred single dose dry powder inhalers include the AEROLIZER™ (Novartis, described in U.S. Pat. No. 3,991,761) and BREEZHALER™ (Novartis, described in U.S. Pat. No. 8,479,730 (Ziegler et al.). Other suitable single-dose inhalers include those described in U.S. Pat. Nos. 8,069,851 and 7,559,325.

Exemplary unit dose blister inhalers include the inhaler described by in US Patent Application Publication 8573197 to Axford et al.

EXAMPLES

Example 1

Spray Drying Equipment and Operations

A spray dryer was used to spray dry the feedstock comprising the plurality of coated particles described herein and for the following examples. The spray dryer configuration comprises a single-nozzle twin-fluid atomizer, a drying chamber, a cyclone, an adaptor, an isolation valve, and a 1-L collector in a temperature-controlled jacket. In many embodiments described herein, the spray drying process may include an atomization process, a drying process, and a particle collection process.

An exemplary atomization process may include the following steps: (A1) a formulated feedstock fluid may be fed through a peristaltic pump to a single-nozzle, air-assisted atomizer mounted in the spray dryer; (A2) compressed dry air with a controlled flow rate is fed to a concentric, convergent gas nozzle; and (A3) expansion of the air at the nozzle tip atomizes the feedstock stream into a fine droplet spray.

The drying process may include the following steps: (B1) drying air heated with an electrical heater is fed to the drying chamber at a controlled flow rate; (B2) the hot drying air interacts with the fine droplet spray from Step A3. The water and an oil medium (e.g., PFOB) in the droplets evaporate, resulting in the formation of solid particles; and (B3) particles and moist air exit the drying chamber at a predetermined temperature.

The particle collection process may include the following steps: (C1) particles and moist air from Step B3 enter the cyclone at high tangential speed; (C2) particles are separated from the air mixture by centrifugal force and are collected at the bottom of the cyclone in a temperature-controlled collection vessel; and (C3) the exhaust air passes through a filter and vents to the atmosphere inside the isolator.

Example 2

Spray dried powders were prepared with equipment and operations as in Example 1, with the materials, parameters, quantities and conditions detailed below. This Example is a suspension-based PulmoSphere formulation prepared by mixing a fine emulsion with cyclosporine seed particles (the seed particles were prepared beforehand by spray drying a solution of cyclosporine dissolved in ethanol):

Feedstock:
Total solids content: 3% w/v
PFOB: 9% v/v
Particle:
Cyclosporin: 70% w/w
DSPC/CaCl$_2$: 30% w/w FIG. 3 is an SEM image depicting cyclosporine seed particles coated with DSPC. The porous surface morphology decreases the density of the particles and improves aerodynamic performance of the powder. In addition, the hydrophobic nature of DSPC also improves the dispersibility of powders by reducing cohesive forces between particles. This surface morphology and reduced cohesive force is common to all particles prepared by embodiments described herein.

The median particle diameter (×50) of the spray dried particles was 2.1 µm, which is within the size range necessary for respirable particles. Emitted dose testing was performed using a capsule-based, dry-powder inhaler (Novartis T-326). Approximately 50 mg of spray dried powder was filled into each #2 HPMC capsule and actuated through the inhaler. For 20 actuations, the mean emitted dose was 95%±2% (one standard deviation). Emitted dose is expressed as a percentage of capsule fill mass; fill mass is the gross weight of the filled capsule minus the weight of empty capsule after the blow-off of the residual powder from the actuated capsule. The MMAD of the emitted aerosol was 3.2 µm (N=3 determinations), and the corresponding fine particle dose (FPD$_{<3.3\ \mu m}$) was 12.1 mg. The FPD$_{<3.3\ \mu m}$ expressed as a percentage of emitted dose was 36%.

Primary Particle Diameter/Size Distribution (Measured Using Laser Diffraction)

| x10 (µm) | x16 (µm) | x50 (µm) | x84 (µm) | x90 (µm) | x99 (µm) | GSD |
|---|---|---|---|---|---|---|
| 0.59 | 0.86 | 2.13 | 3.53 | 4.07 | 11.98 | 2.03 |

Figure 4:
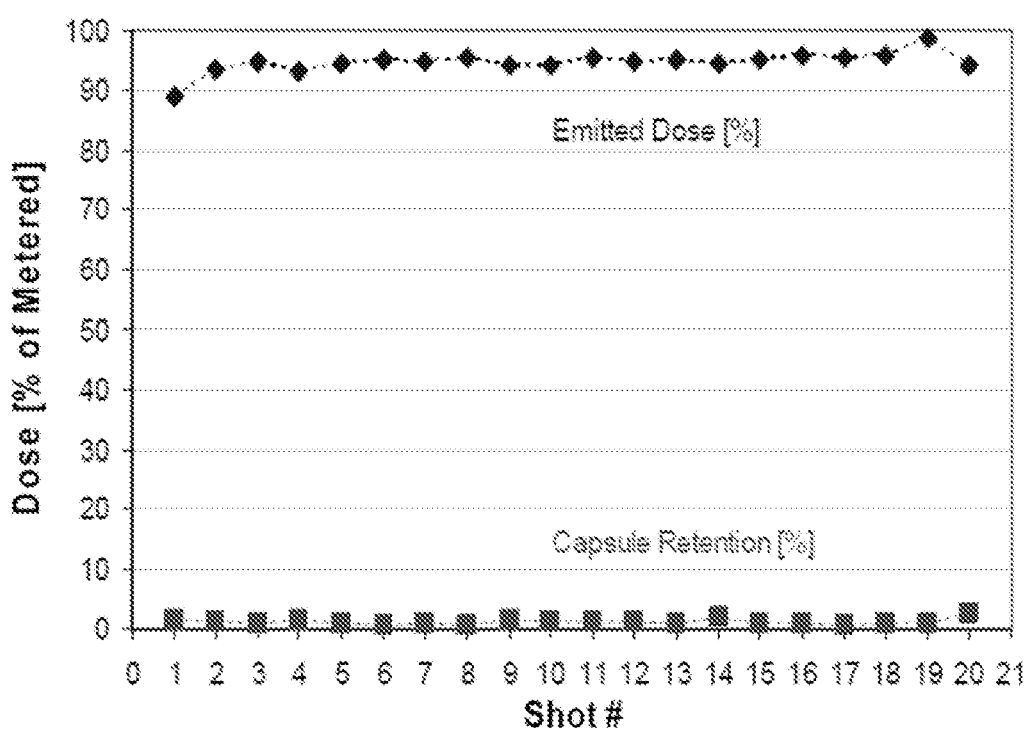
FIG. 4 is a plot illustrating emitted dosage values for individual actuations of a composition containing the coated particles formed in Example 3. Dose retained in the capsule for individual actuations is also plotted.

Emitted Dose, Measured Gravimetrically (See Also FIG. 4)

| Fill Mass mg | Mean ED % | SD % | RSD % |
|---|---|---|---|
| 52.43 | 95 | 2 | 2 |

Figures 5, 6:
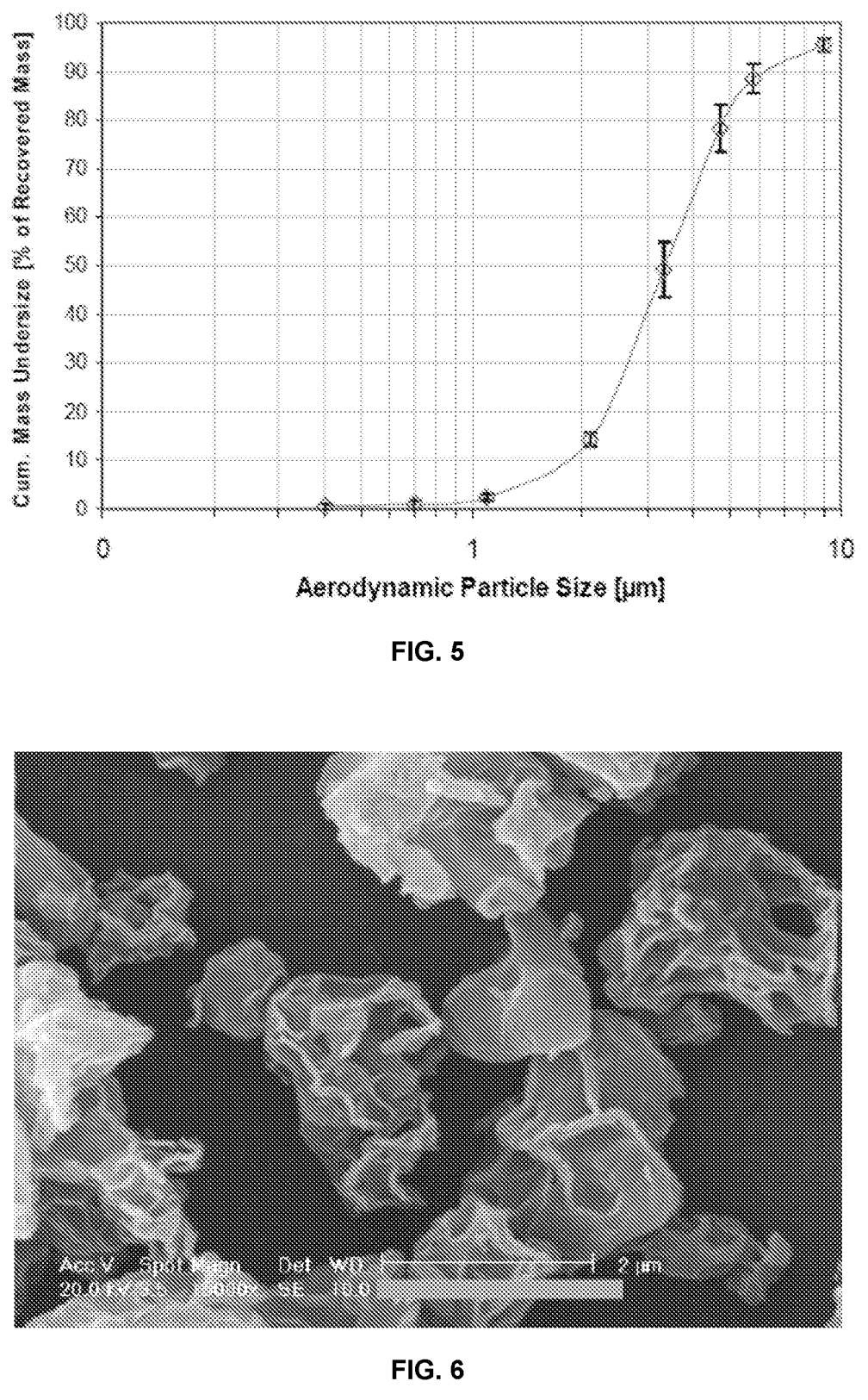

Aerodynamic Particle Size, Measured Gravimetrically (See Also FIG. 5)

| MMAD µm | FPD$_{<3.3\ \mu m}$ mg | FPD$_{<3.3\ \mu m}$ % |
|---|---|---|
| 3.2 | 12.1 | 36 |

FIG. 4 is a graph illustrating emitted dose values for individual actuations, expressed as a % of capsule fill mass (N=20). Dose retained in the capsule for individual actuations is also plotted.

FIG. 5 is a graph illustrating a cumulative size distribution of aerosol recovered on the impactor stages.

Example 3

Spray dried powders were prepared as in Example 1, with the materials, parameters, quantities and conditions detailed below. This example provides a feedstock preparation and spray drying process for preparing coated powders comprising cyclosporine which may be utilized in inhalation formulations. The feedstock is a S-O-W dispersion. The cyclosporine seed particles are first dispersed in PFOB. Following dispersion of the seed particles of drug, a coarse emulsion is prepared by adding the oil phase (comprising the seed particles) into an aqueous dispersion comprising DSPC and $CaCl_2$ using a high-shear mixer (ULTRA-TURRAX® model T-25 mixer). The final feedstock is produced by high-pressure homogenization. This final feedstock comprises an S-O-W dispersion in which the solid seed particles are encapsulated in the oil droplet and the outer surface of the oil phase is stabilized by DSPC/$CaCl_2$.

Feedstock:
Total solids content: 4% w/v;
PFOB: 15% v/v
Particle:
Cyclosporin: 80% w/w
DSPC/$CaCl_2$: 20% w/w.

FIG. 6 is an SEM image that depicts that a solid-in-oil-in-water formulation produces lipid-coated particles with a corrugated surface morphology which results in beneficial powder flow and/or micromeritic properties.

The median particle diameter (×50) of the spray dried particles was 2.1 µm, which is within the size range necessary for respirable particles. Emitted dose testing was performed as described earlier using a T-326 dry-powder inhaler. Approximately 50 mg of spray dried powder was filled into each #2 HPMC capsule and actuated through the inhaler. For 10 actuations, the mean emitted dose was 95%±1% (one standard deviation). The MMAD of the emitted aerosol was 3.1 µm (N=3 determinations), and the corresponding fine particle dose ($FPD_{<3.3\ \mu m}$) was 18.8 mg. The $FPD_{<3.3\ \mu m}$ expressed as a percentage of emitted dose was 46%.

Primary particle diameter/size distribution (measured using laser diffraction)

| x10 (µm) | x16 (µm) | x50 (µm) | x84 (µm) | x90 (µm) | x99 (µm) | GSD |
|---|---|---|---|---|---|---|
| 0.59 | 0.83 | 2.04 | 3.36 | 3.76 | 5.80 | 2.01 |

Figure 7:
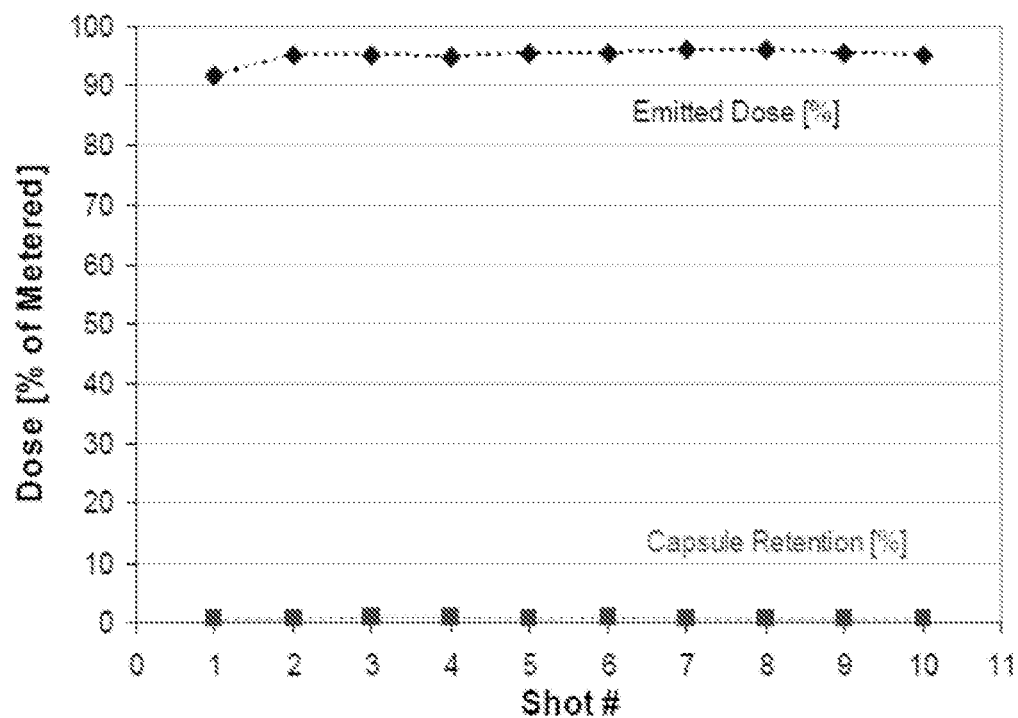
FIG. 7 is a plot illustrating emitted dosage values for individual actuations of a composition containing the coated particles formed in Example 4. Dose retained in the capsule for individual actuations is also plotted.

Emitted Dose, Measured Gravimetrically (See Also FIG. 7)

| Fill Mass mg | Mean ED % | SD % | RSD % |
|---|---|---|---|
| 50.77 | 95 | 1 | 1 |

Figure 8:
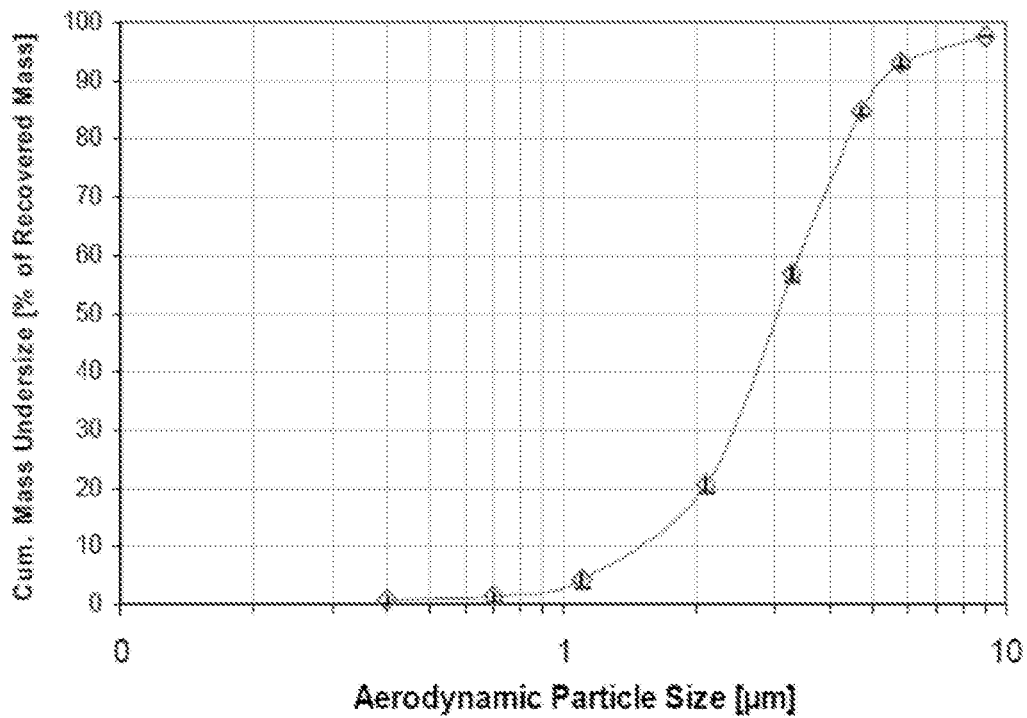
FIG. 8 is a graph illustrating the cumulative size distribution of the recovered aerosol fraction from a composition containing the coated particles formed in Example 4.

Aerodynamic Particle Size, Measured Gravimetrically (See Also FIG. 8)

| MMAD µm | $FPD_{<3.3\ \mu m}$ mg | $FPD_{<3.3\ \mu m}$ % |
|---|---|---|
| 3.1 | 18.8 | 46 |

FIG. 7 depicts a graph that illustrates an emitted dose values for individual actuations, expressed as a % of capsule fill mass (N=10). Dose retained in the capsule for individual actuations is also plotted.

FIG. 8 depicts a cumulative size distribution of aerosol recovered on the impactor stages.

Example 4

Example 4 provides a feedstock preparation and spray drying process for preparing coated powders containing tacrolimus which may be utilized in inhalation formulations. Spray dried powders were prepared as in Example 1, with materials, parameters, quantities and conditions detailed below. Example 4 provides an S/O/W dispersion of the feed stock. The tacrolimus particles are first dispersed in PFOB. Following dispersion of the drug particles, a coarse emulsion is prepared by adding the oil phase (comprising the seed particles) into an aqueous solution comprising DSPC and $CaCl_2$ using a high-shear mixer (ULTRA-TURRAX® model T-25 mixer). The final feedstock is produced by high-pressure homogenization. This final feedstock comprises an S/O/W dispersion in which the solid seed particles are encapsulated in the oil droplet and the outer surface of the oil phase is stabilized by DSPC/$CaCl_2$.

Feedstock:
Total solids content: 1% w/v;
PFOB: 2.4% v/v
Particle:
Tacrolimus: 50% w/w;
DSPC/$CaCl_2$: 50% w/w.

The median particle diameter (×50) of the spray dried particles was 2.0 µm, which is within the size range necessary for respirable particles.

Primary particle diameter/size distribution (measured using laser diffraction)

| x10 (µm) | x16 (µm) | x50 (µm) | x84 (µm) | x90 (µm) | x99 (µm) | GSD |
|---|---|---|---|---|---|---|
| 0.84 | 1.07 | 2.00 | 3.28 | 3.78 | 7.09 | 1.75 |

Example 5

Example 5 provides a feedstock preparation and spray drying process for preparing coated powders containing an epithelial sodium channel blocker which may be utilized in inhalation formulations. Spray dried powders were prepared as in Example 1, with the materials, parameters, quantities and conditions detailed below. Seed particles of the epithelial sodium channel blocker are first dispersed in PFOB. Following dispersion of the drug particles, a coarse emulsion is prepared by adding the oil phase (containing the seed particles) into an aqueous solution containing DSPC and $CaCl_2$ using a high-shear mixer (ULTRA-TURRAX® model T-25 mixer). The final feedstock is produced by high-pressure homogenization. This final feedstock contains an S/O/W dispersion in which the solid seed particles are encapsulated in the oil droplet and the outer surface of the oil phase is stabilized by DSPC/$CaCl_2$.

Feedstock:
Total solids content: 1.5% w/v;
PFOB: 20% v/v
Particle:
Epithelial sodium channel blocker: 74.3% w/w
DSPC/$CaCl_2$: 25.7% w/w.

Figure 9:
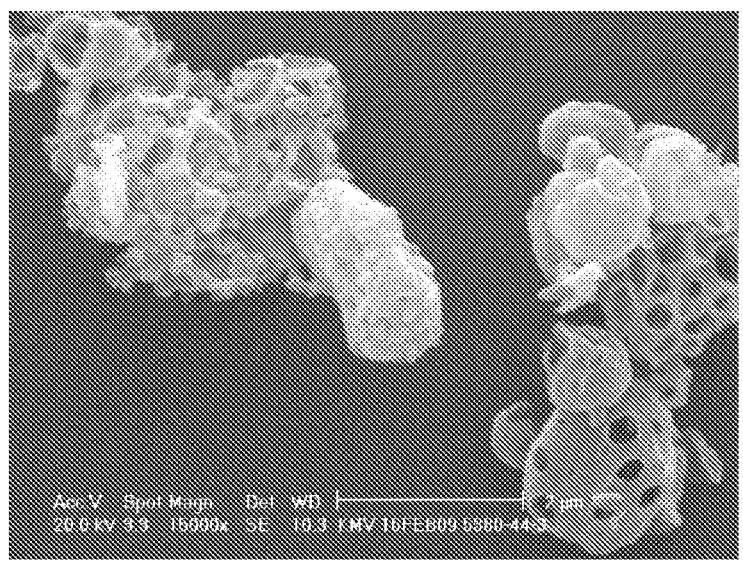
FIG. 9 is an SEM image that depicts that a solid-in-oil-in-water formulation produces lipid-coated particles with a corrugated surface morphology which results in excellent powder fluidization.

When spray-dried, a median particle diameter (×50) of the spray dried particles was 1.79 µm, which is within the size range necessary for respirable particles. Emitted dose testing was performed as described earlier using the T-326 dry-powder inhaler. Approximately 30 mg of spray dried powder was filled into each #2 HPMC capsule and actuated through the inhaler. For 10 actuations, the mean emitted dose was 90%±4% (one standard deviation). The MMAD of the emitted aerosol was 2.5 μm (N=3 determinations), and the corresponding fine particle fraction (FPD<2.8 μm) was 42% and (FPD<4.5 μm) was 58%. FIG. 9 is an SEM photomicrograph of the resulting spray dried power of Example 5, illustrating the particle physical characteristics.

Figure 10:
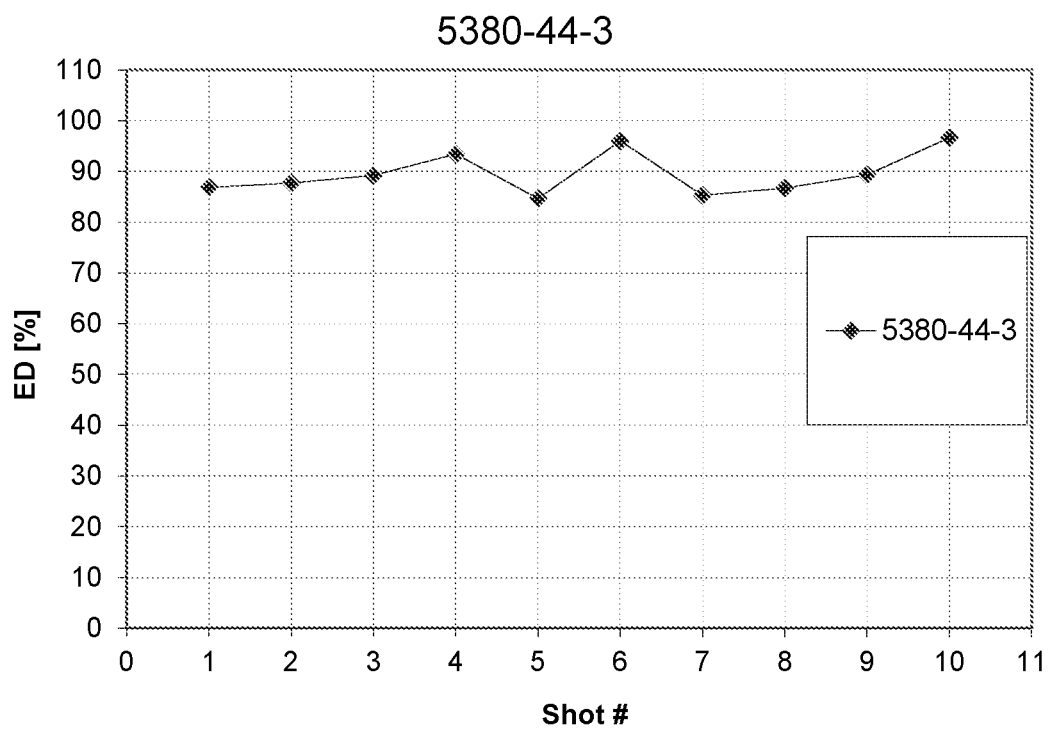
FIG. 10 is a graph that illustrates emitted dose values for individual actuations, expressed as a % of capsule fill mass (N=10).

Emitted Dose, measured gravimetrically. FIG. 10 also illustrates graphically for this Example 5 emitted dose values as a percentage of capsule fill mass.

| Fill Mass mg | Mean ED % | SD % | RSD % |
| --- | --- | --- | --- |
| 29.9 | 90 | 4 | 5 |

Figure 11:
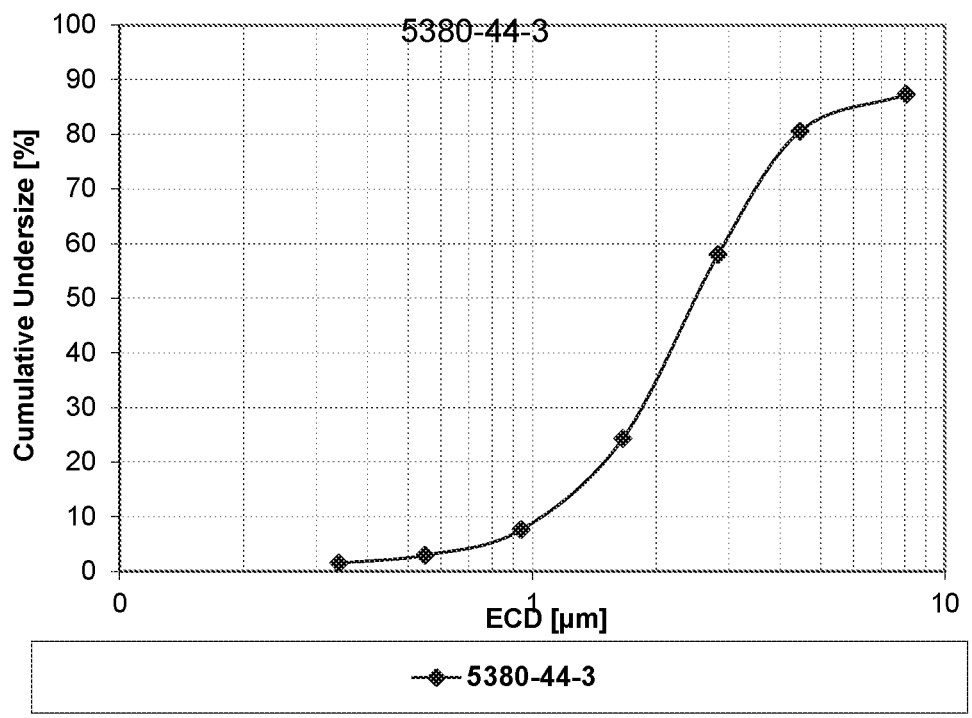
FIG. 11 is a graph depicting a cumulative size distribution of aerosol fraction recovered on the impactor stages.

Aerodynamic Particle Size, measured gravimetrically. FIG. 11 also illustrates for this Example 5 a cumulative size distribution of the aerosol fraction.

| MMAD μm | $FPF_{<2.8\ \mu m}$ % | $FPF_{<4.5\ \mu m}$ % |
| --- | --- | --- |
| 2.5 | 42 | 58 |

Primary particle diameter and size distribution (measured using laser diffraction) of Example 5 is shown in the table below.

| x10 (μm) | x16 (μm) | x50 (μm) | x84 (μm) | x90 (μm) | x99 (μm) | GSD |
| --- | --- | --- | --- | --- | --- | --- |
| 0.68 | 0.88 | 1.79 | 2.95 | 3.35 | 4.90 | 1.83 |

Example 6

Example 6 provides a feedstock preparation and spray drying for preparing coated powders containing indacaterol which may be utilized in inhalation formulations. Spray dried powders were prepared as in Example 1, with the materials, parameters, quantities and conditions detailed below. The indacaterol particles are first dispersed in PFOB. Following dispersion of the drug particles, a coarse emulsion is prepared by adding the oil phase (containing the seed particles) into an aqueous solution containing DSPC and $CaCl_2$ using a high-shear mixer (ULTRA-TURRAX® model T-25 mixer). The final feedstock is produced by high-pressure homogenization. This final feedstock contains an S-O-W dispersion in which the solid seed particles are encapsulated in the oil droplet and the outer surface of the oil phase is stabilized by DSPC/$CaCl_2$.
Feedstock:
Total solids content: 3.0% w/v;
PFOB: 12% v/v
Particle:
QAB 149: 23.1% w/w
DSPC/$CaCl_2$: 76.9% w/w.

The median particle diameter (×50) of the spray dried particles was 1.68 μm, which is within the size range necessary for respirable particles. SEM photomicrography of the resulting spray dried power of Example 6 show the particle physical characteristics, such as corrugated surface morphology, which result from embodiments described herein.

Primary particle diameter/size distribution of Example 6 (measured using laser diffraction) is shown in the table below.

| x10 (μm) | x16 (μm) | x50 (μm) | x84 (μm) | x90 (μm) | x99 (μm) | GSD |
| --- | --- | --- | --- | --- | --- | --- |
| 0.68 | 0.85 | 1.68 | 2.85 | 3.28 | 5.78 | 1.83 |

While the foregoing is directed to embodiments of the invention, other and further embodiments of the invention may be devised without departing from the basic scope thereof, and the scope thereof is determined by the claims that follow.

The invention claimed is:

1. A method for forming particulate agents, the method comprising:
    dispersing hydrophobic seed particles within an oil medium to make an oil phase dispersion;
    making an aqueous dispersion comprising an emulsifier and an emulsion stabilizer;
    adding the oil phase dispersion having hydrophobic seed particles dispersed therein into the aqueous dispersion containing the emulsifier and stabilizer to combine the oil phase dispersion and aqueous dispersion to make an emulsion;
    homogenizing the emulsion to result in a feedstock comprising encapsulated hydrophobic seed particles, oil medium, emulsifier, and emulsion stabilizer; and
    drying the feedstock to form a plurality of coated particles, wherein each coated particle comprises a porous shell disposed over a core, wherein the core comprises at least one of the hydrophobic seed particles.

2. The method of claim 1, wherein the step of drying the feedstock further comprises:
    atomizing the feedstock to generate liquid droplets comprising a discrete phase of encapsulated particles within a continuous aqueous phase;
    drying the liquid droplets at a first temperature within a drying chamber; and
    separating the coated particles from the water vapor.

3. The method of claim 1, wherein the hydrophobic seed particles comprise one or more of a beta-adrenoceptor agonist, a sodium channel blocker, an anti-muscarinic, and mixtures thereof.

4. The method of claim 1, wherein the hydrophobic seed particles comprise indacaterol.

5. The method of claim 1, wherein forming the emulsion further comprises mixing the aqueous dispersion by a high-shear mixing process while adding the oil phase dispersion.

6. The method of claim 1, wherein each of the encapsulated particles comprises a dispersion encompassed by an outer shell, the dispersion comprises at least one of the hydrophobic seed particles and the oil medium, and the outer shell comprises the emulsifier and the emulsion stabilizer.

7. The method of claim 6, wherein substantially all encapsulated particles comprise two or more of the hydrophobic seed particles within the dispersion encompassed by the outer shell.

8. The method of claim 6, wherein a median particle diameter of the encapsulated particles is within a range from about 1.0 μm to about 5.0 μm.

9. The method of claim 1, wherein the porous shell disposed over the core of each coated particle comprises the emulsifier and the emulsion stabilizer.

10. The method of claim 9, wherein the core comprises two or more of the hydrophobic seed particles.

11. The method of claim 9, wherein a median particle diameter of the coated particles is within a range from about 0.5 μm to about 8.0 μm.

12. The method of claim 1, wherein the oil medium comprises a perfluorocarbon medium selected from a group consisting of perfluorooctyl bromide, perfluorooctane sulfonic acid, perfluorobutane, perfluorohexane, perfluorodecalin, mixtures thereof, and combinations thereof.

13. The method of claim 1, wherein the emulsifier comprises a phospholipid compound selected from the group consisting of distearoylphosphatidylcholine (DSPC), dimyristoylphosphatidylcholine (DMPC), diarachidoylphosphatidylcholine (DAPC), dipalmitoylphosphatidylcholine (DPPC), dilauroylphosphatidylcholine (DLPC), dioleoylphosphatidylcholine (DOPC), dibehenoylphosphatidylcholine (DBPC), mixtures thereof, and combinations thereof.

14. The method of claim 1, wherein the emulsion stabilizer comprises at least one compound selected from a group consisting of an inorganic salt, an organic salt, a carbohydrate, an amino acid, mixtures thereof, and combinations thereof.

15. The method of claim 1 wherein substantially all encapsulated particles comprise a dispersion encompassed by an outer shell, the dispersion comprises at least one of the hydrophobic seed particles and the oil medium, and the outer shell comprises the emulsifier and the emulsion stabilizer.

* * * * *